US00PP28780P3

(12) United States Plant Patent
Van Swieten

(10) Patent No.: US PP28,780 P3
(45) Date of Patent: Dec. 19, 2017

(54) ***PHALAENOPSIS* ORCHID PLANT NAMED 'PHALFAMZOL'**

(50) Latin Name: ***Phalaenopsis* hybrid**
Varietal Denomination: PHALFAMZOL

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 62 days.

(21) Appl. No.: 14/999,295

(22) Filed: Apr. 21, 2016

(65) Prior Publication Data

US 2017/0311514 P1 Oct. 26, 2017

(51) Int. Cl.
*A01H 5/02* (2006.01)

(52) U.S. Cl.
USPC ..... Plt./311

(58) Field of Classification Search
USPC ..... Plt./263.1, 311
See application file for complete search history.

(56) References Cited

PUBLICATIONS

UPOV-PLUTO: Plant Vriety Database, Aug. 9, 2017, citation for 'phalfamzol'. 1 page.*
EU Community Plant Variety Rights Application No. 2015/2221, Application n°A201501725, filed Sep. 24, 2015, 8 pages.
EU Community Plant Variety Office Official Gazette, Jun. 2015, Dec. 15, 2015, cover page and pp. 36, 55.

* cited by examiner

*Primary Examiner* — Susan McCormick Ewoldt
*Assistant Examiner* — Karen Redden
(74) *Attorney, Agent, or Firm* — Jondle & Associates, P.C.

(57) ABSTRACT

A new and distinct variety of *Phalaenopsis* plant named 'PHALFAMZOL', particularly characterized by having yellow, brassy colored flowers with light centers, 1 to 3 peduncles that are short to medium long and sturdy, leaves that are oblong, and is propagated by meristem tissue culture, is disclosed.

3 Drawing Sheets

Genus and species: *Phalaenopsis* hybrid.
Variety denomination: 'PHALFAMZOL'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFAMZOL'.

The new *Phalaenopsis* plant is a product of a planned breeding program conducted by the inventor in Bleiswijk, The Netherlands. The objective of this breeding program was to create a new *Phalaenopsis* plant with numerous attractive and unique yellow brassy colored flowers, suitable for potted plant production.

The new *Phalaenopsis* plant 'PHALFAMZOL' is a result of cross-pollination made by the inventor in July 2006 in Bleiswijk, The Netherlands of the proprietary female, or seed parent, *Phalaenopsis* hybrid '12629-0015' (unpatented) with the proprietary male, or pollen parent, *Phalaenopsis* hybrid '22286-0005' (unpatented).

The new *Phalaenopsis* was selected by the inventor as a single plant within the progeny of the stated cross-pollination in a controlled greenhouse in Bleiswijk, The Netherlands in July 2009. Asexual reproduction of the new *Phalaenopsis* plant by meristem tissue culture since 2012 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Sep. 24, 2015. 'PHALFAMZOL' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFAMZOL' as a new and distinct variety of *Phalaenopsis* plant.

1) Yellow, brassy colored flowers with a light center;
2) 1 to 3 peduncles;
3) Peduncle is short to medium long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in January 2016. Colors in the photographs may differ from the color values cited in the detailed botanical description, which accurately describe the actual colors of the new variety.

DESCRIPTION OF THE NEW VARIETY

Figure 1:
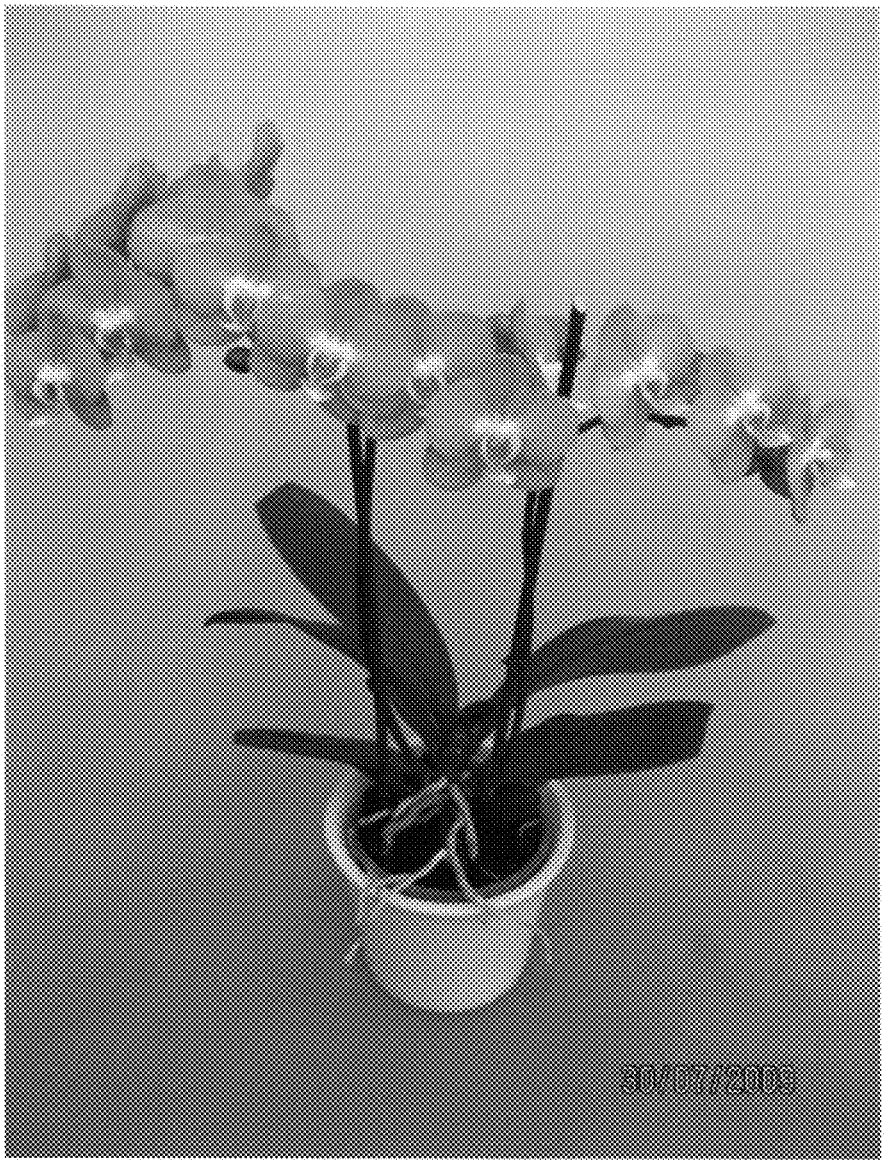
FIG. 1 shows the overall plant habit, including blooms and foliage of 'PHALFAMZOL'.
Figure 2:
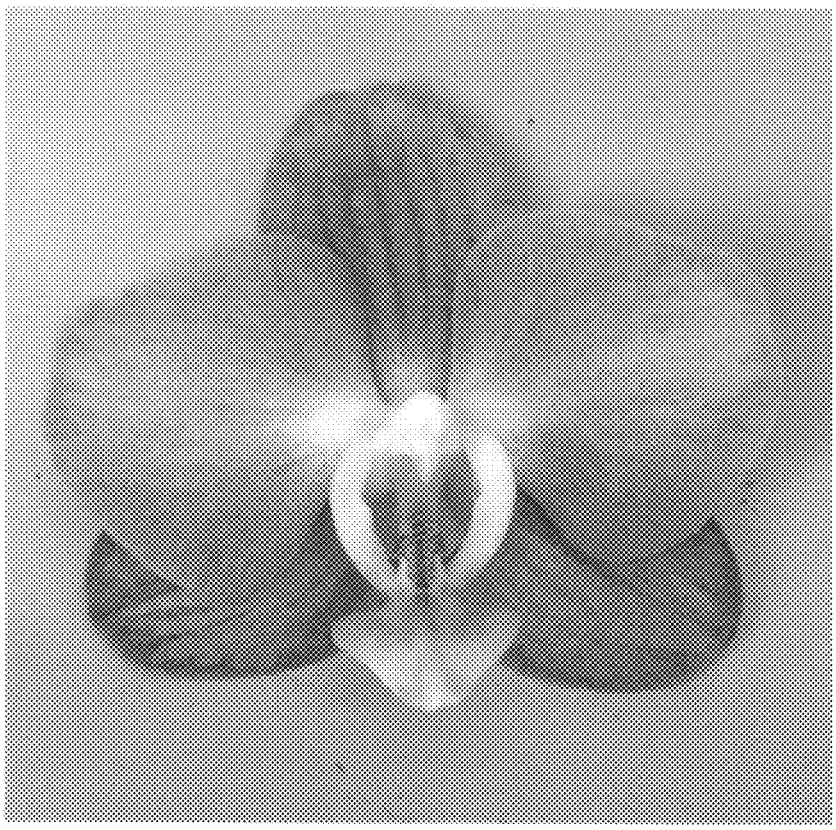
FIG. 2 shows a close-up of a flower of 'PHALFAMZOL'.
Figure 3:
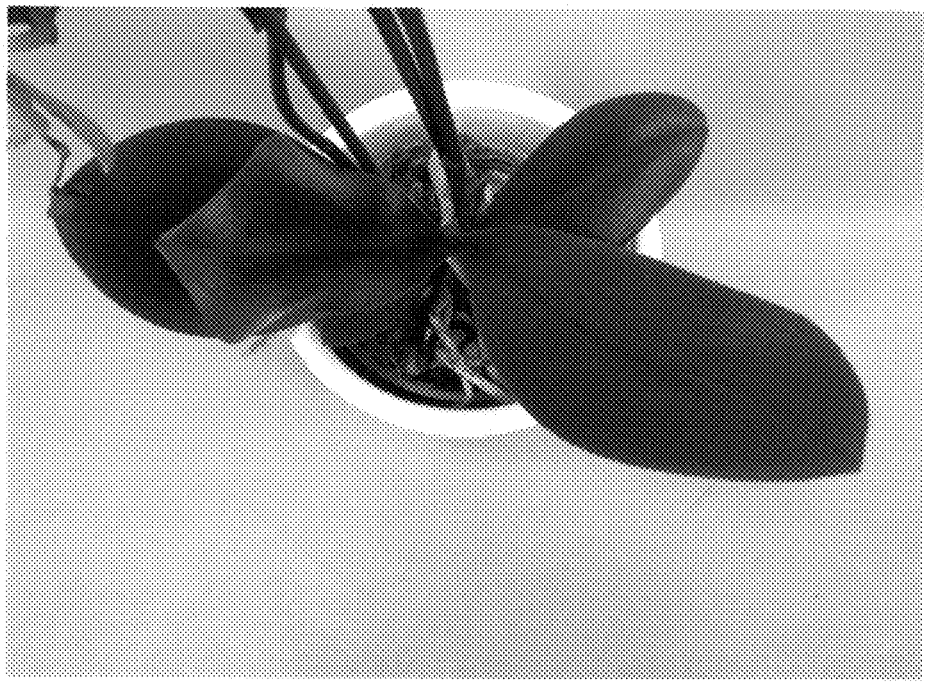
FIG. 3 shows a close-up of the leaves of 'PHALFAMZOL'.

The following detailed description sets forth the distinctive characteristics of 'PHALFAMZOL'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in January 2016 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—*Phalaenopsis*.

*Variety name*.—'PHALFAMZOL'.

Parentage:

*Female parent*.—*Phalaenopsis* cultivar '12629-0015' (unpatented).

*Male parent*.—*Phalaenopsis* cultivar '22286-0005' (unpatented).

Propagation:

*Type*.—Meristem tissue culture.

Roots:

*Root description*.—Greyed-green colored roots with lateral roots having light green colored root tips.

Plant:

*Commercial crop time to flowering*.—Approximately 48 to 50 weeks from a rooted cutting to finish in a 12 cm pot.

*Growth habit of peduncle*.—Standard, green leaves, raceme to panicle.

*Height* (*from soil level to top of inflorescence*).—Approximately 30.0 cm to 40.0 cm.

*Width* (*measured from leaf tips*).—About 23.0 cm to 28.0 cm.

*Vigor*.—Sturdy.

Leaves:

*Mature leaves*.—Quantity per plant: 6 to 8 leaves are produced before flowering. Length (fully expanded): 13.0 cm to 16.0 cm. Width: 5.5 cm to 6.5 cm. Shape: Oblong. Base shape: Moderately elongated. Apex: Unequal obtuse. Leaf blade angle with the petiole (measured from the horizontal position): Between 25 degrees and 60 degrees. Leaf margin: Entire. Color: Upper surface: RHS 147A. Lower surface: RHS 146A. Texture: Smooth. Thickness: 2.0 mm to 2.3 mm. Venation: Pattern: Parallel. Color of the midvein: Upper surface: RHS 147A. Lower surface: RHS 146A.

Peduncle:

*Quantity per plant*.—1 to 3.

*Number of flowers per peduncle*.—8 to 12.

*Length*.—29.0 cm to 34.0 cm.

*Diameter*.—4.3 mm to 4.6 mm.

*Strength*.—Strong.

*Aspect*.—Upright to slightly pendant.

*Texture*.—Smooth.

*Color*.—Mix of green (RHS 146A and 147A) with a touch of brown (RHS 200A).

*Internode length*.—22.0 mm to 32.0 mm.

*Callosities*.—None.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 130.0 mm to 160.0 mm.

*Flowering time*.—First flowers can be expected 10 to 11 months after planting in a 12 cm pot.

*Flower*.—Height: 58.0 mm to 63.0 mm. Diameter: 61.0 mm to 66.0 mm. Depth of lip: 17.0 mm to 19.0 mm.

*Flower longevity*.—On the plant: 12 to 20 weeks.

*Fragrance*.—Absent.

*Flower bud*.—Average size: Medium. Length: 18.0 mm to 20.0 mm. Width: 16.0 mm to 18.0 mm. Shape: Egg shaped. Color: Mix of greyed-green (RHS 146C and 152A) and diluted greyed-red (RHS 183B).

*Petals*.—Arrangement: Open/free. Shape: Semi-circular. Apex: Rounded/emarginated asymmetric. Margin: Slightly undulated. Length (from base to tip): 28.0 mm to 30.0 mm. Width: 33.0 mm to 35.0 mm. Color (when fully opened): Upper surface: Basic color: Yellow-green (RHS 151C); towards the base purple (RHS 75A and 75B) fading to a white center (RHS 155C). Over color: Greyed-red (RHS 181A). Lower surface: Basic color: Yellow/green (RHS 144A and 145C) with a touch of light purple at the base (RHS 75A). Over color: Diluted greyed-purple towards the edge (RHS 181A) and white (RHS 155C) towards the base.

*Dorsal sepal*.—Shape: Broad elliptic. Apex: Emarginated symmetric. Margin: Entire. Length (from base to tip): 32.0 mm to 34.0 mm. Width: 26.0 mm to 28.0 mm. Color (when fully opened): Upper surface: Basic color: Yellow-green (RHS 144A and 151C) fading to white at the base (RHS 155C). Over color: Greyed-red (RHS 181A) fading to white towards the apex. Lower surface: Basic color: Yellow-green (RHS 144A and 151C). Over color: Greyed-red (RHS 183A).

*Lateral sepals*.—Shape: Ovate. Apex: Symmetric. Margin: Entire. Length (from base to tip): 31.0 mm to 33.0 mm. Width: 25.0 mm to 27.0 mm. Color (when fully opened): Upper surface: Basic color: Yellow-green (RHS 144A and 151A). Over color: Greyed-red, fading towards the center (RHS 181A). Lower surface: Basic color: Yellow-green (RHS 152A). Over color: Diluted greyed-red, more intense towards the edge (RHS 183D).

*Labellum* (*lip*).—Margin: Entire. Whiskers: Present. Length of whiskers: 2.0 mm to 4.0 mm. Color of whiskers: Yellow-green (RHS 151D). Pubescence on the lip: Absent.

*Lateral lobe*.—Shape: Weakly spatulate. Length (from base to tip): 12.0 mm to 13.0 mm. Width: 5.0 mm to 7.0 mm. Color: White (RHS 155C) with a touch of yellow on the edge (RHS 3B) and red-purple stripes at the base (RHS 60A).

*Apical lobe*.—Shape: Rhombic. Length: 15.0 mm to 17.0 mm. Width: 14.0 mm to 16.0 mm. Color: Yellow (RHS 12A) with a touch of greyed-orange over color at the base (RHS 173A); mix of yellow-green (RHS 150C) and white (RHS 155C) towards the whiskers.

*Callus*.—Average size: Small. Height: 0.3 cm to 0.4 cm. Length: 0.3 cm to 0.4 cm. Width: 0.4 cm to 0.5 cm. Color: Yellow (RHS 9A), dotted (RHS 185A) and white on the sides (RHS 155C).

Reproductive organs:

*Column*.—Length: 9.0 mm to 11.0 mm. Diameter: 4.6 mm to 4.9 mm. Color: White (RHS 155C) with a touch of lilac (RHS 69C).

*Pollinia*.—Quantity: 2. Size: 8.0 mm to 10.0 mm. Color: Yellow-orange (RHS 21A).

*Ovary*.—Length: 6.0 mm to 9.0 mm. Diameter: 2.3 mm to 2.6 mm.

*Pedicel*.—Length: 27.0 mm to 30.0 mm. Diameter: 2.6 mm to 2.9 mm. Color: Green (RHS 144A), light green (RHS 145B to 145C) and a touch of lilac towards the flower (RHS 157C and 69B).

Disease, pest, and stress resistance: No specific resistance or susceptibility observed to pathogens and pests common to *Phalaenopsis*.

Fruit and seeds: Fruit and seed development has not been observed on plants of the new *Phalaenopsis* to date.

COMPARISON WITH PARENTAL AND COMMERCIAL VARIETIES

'PHALFAMZOL' differs from female parent plant '12629-0015' (unpatented) in that the color of the apical lobe of the lip of 'PHALFAMZOL' is yellow, with a touch of greyed-orange overall color at the base and a mix of yellow-green and white towards the whiskers, whereas the color of the apical lobe of the lip of '12629-0015' is red-purple. Additionally, 'PHALFAMZOL' has more narrow lip whiskers than '12629-0015' and a dotted callus, whereas '12629-0015' has wider lip whiskers than 'PHALFAMZOL' and a striped callus.

'PHALFAMZOL' differs from the male parent '22286-0005' (unpatented) in that the apical lobe of the lip of 'PHALFAMZOL' has a small bump and ridge, whereas the apical lobe of the lip of '22286-0005' has a large bump and ridge. Additionally, the flowers of 'PHALFAMZOL' are narrower than those of '22286-0005' and have no spots, whereas the flowers of '22286-0005' are wider than 'PHALFAMZOL' and are spotted.

'PHALFAMZOL' is most similar to the commercial *Phalaenopsis* plant named 'PHALFYPCI' (U.S. Plant Pat. No. 26,961). 'PHALFAMZOL' differs from commercial variety 'PHALFYPCI' in that the flowers of 'PHALFAMZOL' are yellow-green, fading to white centers and the columns are white with a touch of lilac, whereas the flowers of 'PHALFYPCI' are orange with purple centers and the columns are purple. Additionally, the color of the apical lobe of the lip of 'PHALFAMZOL' is yellow, with a touch of greyed-orange over color at the base and a mix of yellow-green and white towards the whiskers, while the color of the apical lobe of the lip of 'PHALFYCPI' is greyed-red with purple towards the whiskers with a touch of yellow at the base.

A new and distinct variety of *Phalaenopsis* plant named 'PHALFAMZOL', particularly characterized by having yellow, brassy colored flowers with light centers, 1 to 3 peduncles that are short to medium long and sturdy, leaves that are oblong, and is propagated by meristem tissue culture, is disclosed.

I claim:

1. A new and distinct variety of *Phalaenopsis* plant named 'PHALFAMZOL', substantially as described and illustrated herein.

* * * * *